United States Patent
Enzelberger

(10) Patent No.: US 8,551,733 B2
(45) Date of Patent: Oct. 8, 2013

(54) PRODUCTION OF OLIGOCLONAL MIXTURES OF IMMUNOGLOBULINS IN SINGLE CELLS

(75) Inventor: Markus Enzelberger, Munich (DE)

(73) Assignee: MorphoSys AG, Martinsried / Planegg (DE)

( * ) Notice: Subject to any disclaimer, the term of this patent is extended or adjusted under 35 U.S.C. 154(b) by 89 days.

(21) Appl. No.: 13/147,383

(22) PCT Filed: Feb. 8, 2010

(86) PCT No.: PCT/EP2010/051469
§ 371 (c)(1),
(2), (4) Date: Aug. 2, 2011

(87) PCT Pub. No.: WO2010/089387
PCT Pub. Date: Aug. 12, 2010

(65) Prior Publication Data
US 2012/0028302 A1 Feb. 2, 2012

Related U.S. Application Data

(60) Provisional application No. 61/150,819, filed on Feb. 9, 2009.

(30) Foreign Application Priority Data

Feb. 9, 2009 (EP) ..................................... 09152379

(51) Int. Cl.
C12P 21/06 (2006.01)

(52) U.S. Cl.
USPC ....................................................... 435/69.1

(58) Field of Classification Search
USPC ....................................................... 435/69.1
See application file for complete search history.

(56) References Cited

U.S. PATENT DOCUMENTS

| | | | |
|---|---|---|---|
| 5,877,018 | A | 3/1999 | Filmus |
| 6,933,378 | B2 | 8/2005 | Atabekov |
| 7,429,486 | B2 | 9/2008 | VanBerkel |
| 2005/0059082 | A1 | 3/2005 | Breitling |
| 2007/0059766 | A1 | 3/2007 | Logtenberg |
| 2007/0243225 | A1 | 10/2007 | McKay |
| 2009/0263864 | A1 | 10/2009 | VanBerkel |

FOREIGN PATENT DOCUMENTS

| | | |
|---|---|---|
| EP | 0633941 | 1/1995 |
| WO | 8900603 | 1/1989 |
| WO | 0009704 | 2/2000 |
| WO | 0039300 | 7/2000 |
| WO | 02100387 | 12/2002 |
| WO | 03101189 | 12/2003 |
| WO | 2008145133 | 12/2008 |

OTHER PUBLICATIONS

Cunningham et al. 1998; Genes and enzymes of carotenoid biosynthesis in plants. Annual Review of Plant Phisology and Plant Molecular Biology. 49: 557-583.*
Zhang et al. 2008; Heteromer formation of a long-chain prenyl diphosphate synthase from fission yeast Dps1 and budding yeast Cpq1. FEBS Journal 275(14): 3653-3668.*
Liyan Chen, et al.: "Expression of a prototypic anti-colorectal cancer polyclonal antibody library in mammalian cells"; 2003 Elsevier Science B.V., Immunology Letters 88 (2003) pp. 135 to 140.
John S. Haurum: "Recombinant polyclonal antibodies: the next generation of antibody therapeutics?" 2006 Elsevier Ltd., Drug Discovery Today, vol. 11, Nos. 13/14, Jul. 2006, pp. 655 to 660.
John S. Haurum, et al.: "Recombinant polyclonal antibodies: Therapeutic antibody technologies come full circle"; IDrugs 2005 8(5): 404-409.
Mimi C. Sammarco, et al.: "A series of bidirectional tetracycline-inducible promoters provides coordinated protein expression"; 2005 Elsevier; Bidirectional tetracycline-inducible promoters / M.C. Sammarco, E. Grabczyk / Anal. Biochem. 346 (2005) 210-216.
Sharon, et al.: "Recombinant Polyclonal Antibody Libraries"; Combinatorial Chemistry & High Throughput Screening, 2000, pp. 185 -196.
Sharon, et al.: "Recombinant Polyclonal Antibodies for Cancer Therapy"; Journal of Cellular Biochemistry 96:305-313 (2005).
Suchandra Deb Roy, et al.: "Generation of marker free salt tolerant transgenic plants of Arabidopsis thaliana using the gly I gene and cre gene under inducible promoters"; Plant Cell Tiss Organ Cult (2008) 95:1-11.
Finn C. Wiberg, et al.: "Production of Target-Specific Recombinant Human Polyclonal Antibodies in Mammalian Cells"; 2006 Wiley Periodicals, Inc.
PCT/EP2010/051469 International Preliminary Report on Patentability.

* cited by examiner

Primary Examiner — Karen Cochrane Carlson

(57) ABSTRACT

The present invention provides methods to produce mixtures of exogenous proteins in single cells. Preferably said exogenous proteins are heteromeric and multimeric proteins, such as immunoglobulins. The method enables the controlled expression of proteins, thereby allowing the correct formation and assembly of multimeric proteins, such as immunoglobulins.

13 Claims, 2 Drawing Sheets

PRODUCTION OF OLIGOCLONAL MIXTURES OF IMMUNOGLOBULINS IN SINGLE CELLS

CROSS-REFERENCE TO RELATED APPLICATION

Figure 1:
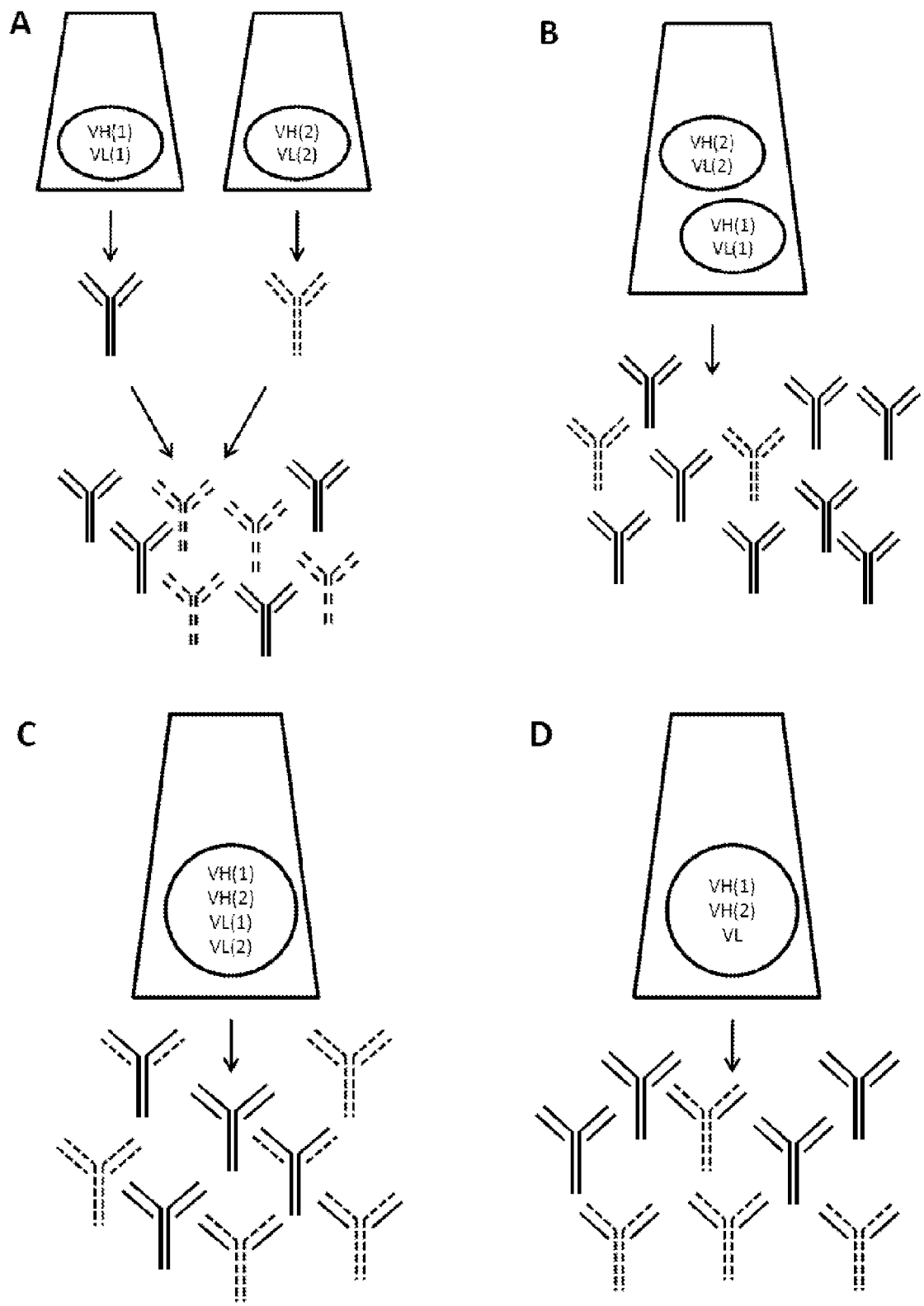

This application claims the benefit of U.S. provisional application Ser. No. 61/150,819 filed Feb. 9, 2009, which is incorporated by reference in its entirety.

BACKGROUND OF THE INVENTION

Oligoclonal and polyclonal binding-pair member mixtures are valuable tools in the treatment of disease, especially infectious disease and cancer. Employing a composition containing a plurality of binding-pair members that bind to more than one epitope can increases the efficiency of respective compositions, and decrease the risk of epitope escape, for example. Such immunoglobulin mixtures furthermore enable the targeting of different pathogens or specific subfamilies or subspecies of a certain pathogen or a certain cell population, especially in circumstances where the generation of cross-reactive antibodies is not possible or not desirable.

Several strategies for the production of oligoclonal and polyclonal binding-pair members, such as antibody mixtures, exist. In its easiest form each single antibody is produced from a separate cell line, i.e. each antibody is produced from a single cell line in separate growth vessels, typically fermenters. Thereafter, the individual antibodies are mixed afterwards to form the oligoclonal or polyclonal antibody mixture. See panel A in FIG. 1. As is evident, this approach requires many resources and is therefore commercially unattractive.

In another approach, each antibody is still produced from a separate cell line, but the cell lines are mixed in one growth vessel, typically a fermenter. This approach has the shortcomings that it is essentially impossible to control the growth of different cell lines in one fermenter, thereby rendering production more or less to a gamble. These issues get even more complicated if more than two antibodies are produced, since some cell line might be able to out-grow others, thereby suppressing the production of some immunoglobulins of the mixture. See for example WO2008/145133. This approach is depicted in panel B in FIG. 1.

In yet another approach, two or more antibodies are produced in the same cell line, which a fortiori takes place in one growth vessel. The disadvantage of this approach hails from the heterodimeric nature of the immunoglobulins. The variable heavy chain of one antibody will not only pair with its "own", designated variable light chain, but also undesirably with the variable light chain of the second (or any further, subsequent) antibody produced by the host cell. This situation gets even more complicated if more than two antibodies are produced by such host cell. The antibodies formed by incorrectly paired immunoglobulin chains may outnumber the number of correctly formed antibodies, and hence this approach is also nothing but an inadequate solution. See panel C in FIG. 1.

Finally, another approach uses "dummy", common light chains (see U.S. Pat. No. 7,429,486). In this approach the specificity of the antibody comes from the variable heavy chain; and the light chain common to all antibodies produced in this system is merely a means to provide a full length immunoglobulin. However, since all antibodies need to be functionally active, the use of a common light chain goes along with a reduction of the types and properties of the immunoglobulins that can be produced. Furthermore, the production of the different heavy chain cannot be adequately controlled, leading to a more or less uncharacterized mixture of immunoglobulins. See panel D in FIG. 1.

Taken together, there is still no satisfactory way to efficiently produce a polyclonal or oligoclonal mixture of immunoglobulins. As will be evident, the methods disclosed in the present invention are not just applicable to immunoglobulins, but to all heteromeric multimeric proteins.

SUMMARY OF THE INVENTION

The present invention for the first time enables the efficient and controllable production of multimeric proteins, such as immunoglobulins, from single host cells in one growth vessel. The present invention provides a method which enables the separation of the production of one multimeric protein from the production of any number of additional multimeric proteins. Since the expression of the genes encoding the different multimeric proteins can be temporally separated, in a preferred embodiments the subunits of a common multimeric protein will bind to each other without substantially binding to a subunit from a different multimeric protein, thereby forming the intended multimeric protein. Improper pairing of polypeptides, leading to the formation of unwanted and undesirable multimeric proteins is therefore circumvented.

The present invention provides a method for the production of at least two exogenous proteins in a eukaryotic host cell, wherein each of the genes encoding said proteins is under the control of a distinct inducible eukaryotic promoter, said method comprising (a) culturing said eukaryotic host cell under conditions that allow the expression of a gene encoding a first exogenous protein, and, (b) culturing said eukaryotic host cell under conditions that allow the expression of a gene encoding a second exogenous protein. The genes encoding said first and said second exogenous proteins are expressed in a temporally separated manner, i.e. during the expression of the gene encoding said first exogenous protein the gene encoding said second exogenous protein is not expressed. Likewise, during the expression of the gene encoding said second exogenous protein the gene encoding said first exogenous protein is not expressed. Said first, said second, as well as each of any potential further exogenous proteins, may be encoded by genes on the same or by genes on different vectors. The host cell may be transfected with said vector or vectors in a transient manner or via stable transfection, e.g. via recombination, such site specific integration.

Figure 2:
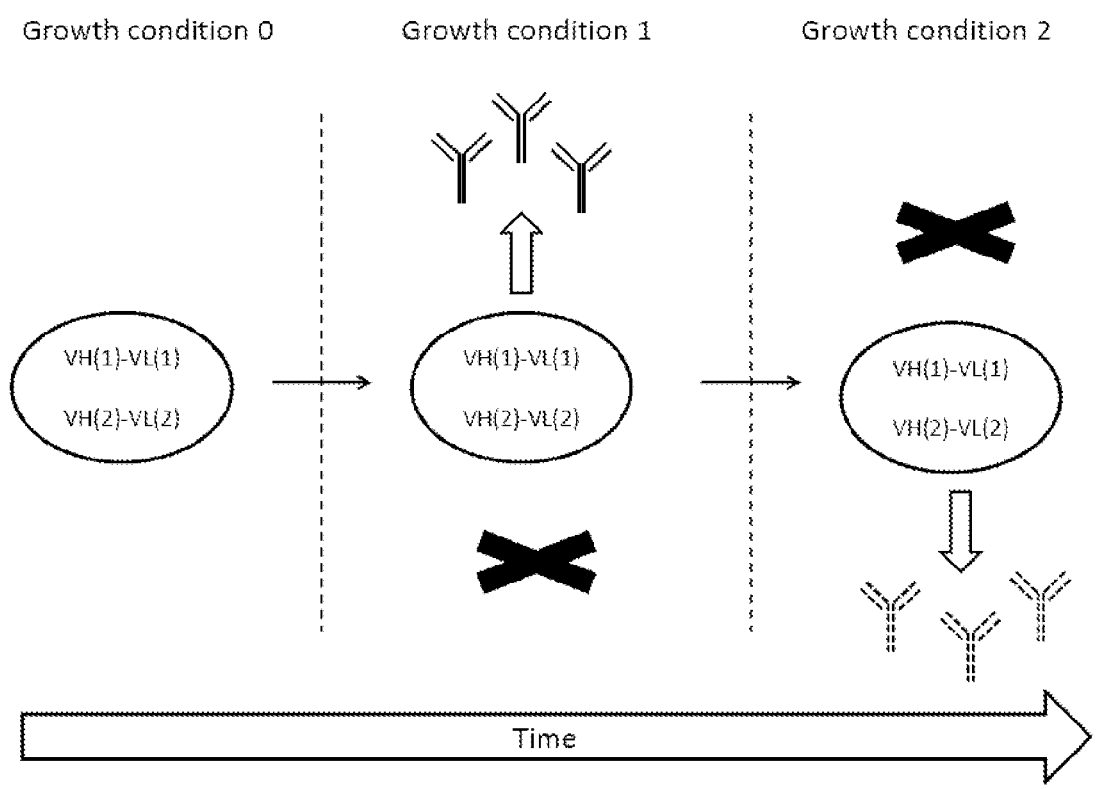

The inventive concept is depicted in FIG. 2. The present invention is particularly useful for the production of multimeric proteins. Such multimeric proteins may be proteins comprising at least one antigen binding site, such as immunoglobulins.

The present invention also provides host cells and vectors to be used in the methods disclosed herein. Furthermore, the present invention also provides mixtures of at least two exogenous proteins obtainable by the methods of the present invention, as well as the use of such mixtures in therapy. The present invention also provides reaction vessels, such as fermenters, for use in the methods of the present invention. The present invention also provides a kit, comprising (a) a host cell comprising the vectors according to the present invention, and (b) instructions to use the said host cells in accordance with the methods described herein.

FIGURE LEGENDS

FIG. 1 depicts the currently available approaches for the production of oligoclonal or polyclonal antibodies. As described herein, the present invention is superior over similar methods known in the prior art. For the sake of simplicity, FIG. 1 only shows a scenario in which two antibodies are produced. The trapezoid structure indicates a growth vessel, such as a culture flask. The ovals and the circles indicate host cells. VH and VL indicate that the respective cells encode for and produce the respective variable heavy and variable light chains. The numbers in brackets intend to differentiate the different variable heavy and variable light chains produced. The first (1) heavy and light chains are represented by solid lines. The second (2) heavy and light chains are represented by dashed or dotted lines. The different strategies are explained in more detail in the "Background" section herein above.

FIG. 2 depicts the strategy of the present invention. A host cell transformed with both VH and VL genes of the present invention. Under certain growth conditions ("Growth condition 0") no VH and VL genes are transcribed. Upon shift to other growth conditions ("Growth condition 1"), the VH and VL genes encoding for one, and only one, antibody are transcribed and the respective antibody is produced by the host cell. The VH and VL genes encoding for the second antibody are not transcribed (black cross). Upon shift to yet other growth conditions ("Growth condition 2"), the VH and VL genes encoding for the second, and only the second, antibody are transcribed and the respective antibody is produced by the host cell. The VH and VL genes encoding for the first antibody are no longer transcribed (black cross).

DETAILED DESCRIPTION OF THE INVENTION

The present invention provides methods for the production of at least two exogenous proteins in a eukaryotic host cell, wherein each of said proteins is under the control of a distinct inducible eukaryotic promoter, said method comprising (a) culturing said eukaryotic host cell under conditions that allow the expression of a gene encoding a first exogenous protein, and, (b) culturing said eukaryotic host cell under conditions that allow the expression of a gene encoding a second exogenous protein.

The term "polypeptide" is used herein in its broadest sense as appreciated by the skilled artisan. Polypeptides comprise at least two amino acids linked via a peptide bond. Typically, polypeptides comprise more than 30 amino acids. Polypeptides of particular interest in connection with the present invention are molecules comprising at least one antigen binding site.

The term "protein" is also used herein in its broadest sense as appreciated by the skilled artisan. A protein comprises one or more polypeptides, where at least part of the polypeptide has or is able to acquire a defined three-dimensional structure arrangement by forming secondary, tertiary, or quaternary structures within and/or between its polypeptide chain(s). Proteins may be monomeric (composed of one polypeptide chain) or multimeric (composed of two or more polypeptide chains). Multimeric proteins may be homomeric (composed of several identical polypeptide chains) or heteromeric (composed of several polypeptide chains, wherein at least two of these polypeptide chains are different).

The terms "exogenous" and "heterologous" are used herein as synonyms, and refer to nucleic acids, polypeptides or proteins which are not naturally occurring in a given host cell. Typically, exogenous or heterologous nucleic acids, polypeptides and proteins are artificially introduced into the host cell. They may originate from a source foreign to a particular host cell or, if from the same source, are modified from their original form.

The term "host cell" as used herein may be any of a number of commonly used cells in the production of exogenous polypeptides or proteins. Preferred host cells of the present invention are eukaryotic host cells, such as fungi cells, yeast cells, plant cells, insect cells or mammalian cells. Most preferred are mammalian host cells. In yet further preferred embodiments said mammalian host cell is selected from a CHO cell (European Collection of Cell Culture; ECACC #85050302), a PER.C6 cell (Crucell, Leiden, The Netherlands), a HKB11 cell (Bayer HealthCare, Berkley/Calif., USA) and a HEK293 cell (American Type Culture Collection; Order no. CRL-1573). Other preferred host cells are yeast cells. In yet other preferred embodiments said yeast host cells are selected from *Pichia pastoris* cells and *Saccharomyces cerevisiae* cells.

The term "promoter" as used herein refers to an untranslated DNA sequence usually located upstream of the coding region that contains the binding site for a DNA-dependent RNA polymerase and initiates transcription of the DNA. The promoter region may also include other elements that act as regulators of gene expression. A promoter includes the transcription initiation site, and binding sites for transcription initiation factors and RNA polymerase, and can comprise various other sites (e.g., enhancers), at which gene expression regulatory proteins may bind.

Other "regulatory regions" that may be involved in driving transcription and controlling (i.e., regulating) the timing and level of transcription of a given DNA sequence, such as a DNA coding for a protein or polypeptide, include, for example, a 5' regulatory region (a DNA sequence located upstream, i.e. 5', of a coding sequence and which comprises the promoter and the 5'-untranslated leader sequence), and a 3' regulatory region (a DNA sequence located downstream, i.e. 3', of the coding sequence and which comprises suitable transcription termination (and/or regulation) signals, including one or more polyadenylation signals).

The various promoters used in accordance with the present invention are "distinct" in the sense that different stimuli lead to the expression of the gene under the control of each promoter. This is a prerequisite for the possibility to induce expression of the proteins under the control of each of said promoters at any given time point.

The term "inducible" as used herein in the context of promoters refers to a promoter which can be activated by addition of a particular molecule or a particular agent or by exposing to physical conditions such as irradiation, light or heat.

Various inducible promoters are known in the art. Inducible promoters include promoters selected from hormone-responsive promoters, metal-responsive promoters, heat shock-responsive promoters, interferon-responsive promoters and antibiotic-responsive promoters. Addition of appropriate inducers leads to the expression from the respective promoters.

In certain preferred embodiments of the present invention the inducible promoter is a hormone-responsive promoter. Hormone-responsive promoters promote transcription only when exposed to a hormone. Examples of hormone-responsive promoters include, but are not limited to: probasin (which is responsive to testosterone and other androgens); MMTV promoter (which is responsive to dexamethazone, estrogen, and androgens); and the whey acidic protein promoter and casein promoter (which are responsive to estrogen). Examples of hormone-responsive promoters are the GRE (glucocorticoid response element) promoter and the ecdyson promoter.

In other preferred embodiments of the present invention, the inducible promoter is a metal-responsive promoter. Metal-responsive promoters are induced in the presence of one or more metals, for example heavy metals. Metal-responsive promoters may be selective for uranium, cadmium, plutonium, or chromium ions. One example of a metal-responsive promoter is the metallothionein promoter.

In other preferred embodiments of the present invention, the inducible promoter is a heat shock-responsive promoters. Heat shock-responsive promoters are induced by increased temperature. Heat shock-responsive promoters known in the art include the Hsp70 promoter.

In other preferred embodiments of the present invention, the inducible promoter is an interferon-responsive promoter. Interferon-responsive promoters can be found in various genes up-regulated upon the action interferon. See for example Kuhn et al (1995) Science, 269, 1427-9.

In other preferred embodiments of the present invention the inducible promoter is a antibiotic-responsive promoter. Best known is the tet promoter, which is up-regulated upon the addition of the antibiotic tetracycline. See for example Shockett et al. (1995) Proc. Natl. Acad. Sci. USA, 92, 6522-6.

Preferred promoters according to the present invention are tight promoters or substantially tight promoters. The term "tight" as used herein in the context of promoters, refers to promoters which are highly stringent, in the sense that no, or substantially no, expression occurs when the promoter is not induced. The expression level of a tight promoter in its non-induced state is at least 10-fold, more preferably at least 20-fold, even more preferably at least 50-fold, even more preferably at least 100-fold, and most preferably at least 1000-fold lower than the expression level of the promoter in its induced state.

The term "conditions that allow the expression [of a polypeptide]" as used herein refers to conditions that lead to the expression of a given polypeptide. The purposefully selection of the conditions of the host cell enables the switching on (or the shut down) of the expression of the polypeptides of the present invention. Typically such change of conditions is brought upon by the addition of a chemical or a naturally occurring compound, an "inducer", to the growth medium of the host cell. Depending on the specific promoter used the nature of the inducer varies. Other changes of conditions that may lead to the expression of polypeptides are an increase of temperature or an exposure to light or to UV.

Inducible promoters have been used in plant cells (see Roy et al; Plant Cell Tiss Organ Cult (2008) 9, 1-11). However, the proteins expressed in Roy et al. were of much less complexity and also served an entirely different purpose. Without elaborating any further on the difficulties to transform experimental data from plant cells to other eukaryotic cells, such as mammalian cells, the present invention furthermore enables the expression and production of several heteromeric proteins, such as immunoglobulins, whereas Roy et al. only produced monomeric proteins. A problem solved by the present invention therefore lies in the production of mixtures of heteromeric proteins, characterized therein that the heteromeric proteins are correctly "paired", i.e. the correct subunits arrange to form the individual hetromeric proteins. Additionally, the two proteins under the control of the inducible promoter in Roy et al. serve a different purpose: Glyoxalase I is a protein which confers salt tolerance to transgenic *Arabidopsis thaliana* plants, whereas the second gene, Cre recombinase, is a genetic tool which is used to remove the selectable marker gene. That said, the functionality of the proteins produced in Roy et al. are entirely different, whereas in the present invention it is exactly a well defined mixture of heteromeric polypeptides (oligoclonal or polyclonal antibodies) that are produced. This is enabled through the temporal separation of gene expression in accordance with the present invention.

The term "subsequently" as used herein refers to a temporal separation of the expression of the genes, and hence the production of the polypeptides of the present invention, which are under the control of different inducible promoters.

As the need may be, in certain circumstances it may also be useful that two or more genes encoding said polypeptides are expressed at the same time. Therefore, in certain situations it might not be required that the temporal separation of the expression of the genes is maintained over the entire growth of the host cell in the growth vessel.

In preferred embodiments the present invention provides a method for the production of at least two exogenous proteins in a eukaryotic host cell, wherein each of the genes encoding said proteins is under the control of a distinct inducible eukaryotic promoter, said method comprising (a) culturing said eukaryotic host cell under conditions that allow the expression of a gene encoding a first exogenous protein, and, (b) culturing said eukaryotic host cell under conditions that allow the expression of a gene encoding a second exogenous protein. In certain preferred embodiments the conditions that allow the expression of the gene encoding the first exogenous protein in step (a) do not, or substantially do not, lead to the expression of the gene encoding the second exogenous protein. Vice versa, the conditions that allow the expression of the gene encoding the second exogenous protein in step (b) do not, or substantially do not, lead to the expression of the gene encoding the first exogenous protein. However, as already mentioned above, conditions may be selected that lead to the expression of both the first and the second (or even additional) exogenous proteins. Therefore, in certain embodiments, the present invention provides methods, in which during the expression of said gene encoding the first exogenous protein in step (a), said gene encoding the second exogenous protein is essentially not expressed. Also, in other embodiments during the expression of said gene encoding the second exogenous protein in step (b), said gene encoding the first exogenous protein is essentially not expressed.

"Essentially not expressed" as used in the present invention, refers to a situation in which the gene encoding a given polypeptide or protein is not expressed or only expressed at minimal threshold levels. Such expression levels are contrasted by induced expression levels, i.e. conditions under which the host cell of the present invention does produce the polypeptides or proteins. Conditions under which a polypeptide or protein is not expressed aim at keeping the expression level as low as technically feasible. In a preferred case the respective promoters are tight at such conditions, but it will be appreciated that this is not always completely possible in biological systems, thereby making some degree of tolerance acceptable.

The term "growth vessel" refers to any means that may be used to grow the host cells of the present invention. Depending on the exact nature of the host cell used, different growth vessels may be used as well. Respective choices will be obvious to the skilled artisan. Typical growth vessels to be used in the present invention include flasks, roller bottles, bioreactors and fermenters.

In certain embodiments of the present invention, the said first and said second exogenous protein are encoded by genes on different vectors. In such cases, the host cell will need to be transfected with both vectors. Alternatively, and preferably, said first and said second exogenous protein are encoded by genes on the same vector. In the latter case the host cell only needs to be transfected with one vector.

The host cell may be transfected a the vector (or vectors) of the present invention by any conventional means known to the skilled artisan. For example transfection may be a transient transfection. Therefore in certain embodiments of the present invention one or both of said genes encoding said exogenous proteins is/are introduced into said eukaryotic host cell via transient transfection.

Alternative, and preferably, the host cells are transfected via stable transfection. Therefore in certain embodiments of the present invention one or both of said genes encoding said exogenous proteins is/are introduced into said eukaryotic host cell via stable transfection. In this type of transfection the genetic material that is introduced into the host cell is retained beyond reproduction, since the genetic material is stably integrated into the genome of the host cell. Typically the integration into the genome of the host cell occurs via a recombination event. Such a recombination event may occur randomly, or may be directed by experimental means. Several systems are known in the art that enable the site specific integration of nucleic acids into the genome of a host cell. Therefore, in certain embodiments of the present invention one or both of said genes encoding said exogenous proteins is/are introduced into said eukaryotic host cell via site specific integration. In certain embodiments said stable integration is affected by site specific integration. Site specific integration has the advantage that the site of integration is known, and hence unwanted side effects are minimized.

Site specific integration systems that can be used in conjunction with the present invention are known in the art. Two exemplary systems that may be used are the cre/lox system and the Flp-In system. Therefore, in certain embodiments of the present invention said side specific integration is side specific integration via the cre/lox system or via the Flp-In system.

The cre/lox system is a site specific recombination system making use of the Cre protein, a site-specific DNA recombinase. Cre can catalyse the recombination of DNA between specific sites in a DNA molecule. These sites, known as loxP sequences, contain specific binding sites for Cre that surround a directional core sequence where recombination can occur. See e.g. Biochem Biophys Res Commun, 237(3), 752-757. The Flp-In system (Invitrogen, Carlsbad/Calif., USA) makes use of a Flp Recombination Target (FRT) site, at which site-specific recombination of respective tailor-made donor DNA molecules occurs. These and other similar recombination systems are known and can be used in conjunction with the present invention.

The first and/or the second exogenous protein produced in accordance with the present invention is preferably a multimeric protein. Even more preferably, a multimeric protein is a heteromeric multimeric protein. The advantages of the presented invention become particularly clear when such heteromeric multimeric proteins are expressed and produced by the host cell. The possibility to temporally separate the expression of the various subunits of a first heteromeric multimeric protein from the expression of the various subunits of a second heteromeric multimeric protein enable the correct assembly of the respective subunits of each such heteromeric multimeric protein. Therefore, in certain embodiments of the present invention the first and/or the second exogenous proteins is a multimeric protein. In more preferred embodiments both, the first and the second exogenous protein, is a multimeric protein. In even more preferred embodiments the first and/or the second exogenous proteins is a heteromeric multimeric protein. In most preferred embodiments, both the first and the second exogenous protein are heteromeric multimeric proteins.

Preferred multimeric proteins, e.g. heteromeric multimeric proteins, are proteins which comprise at least one antigen binding site, such as immunoglobulins. In line with the preceding paragraph, the present invention warrants and essentially guarantees that, if desired, the correct variable light chain may will pair with the correct variable heavy chain, and not with a variable heavy chain of another immunoglobulin. In particular, the variable light chain of the first exogenous immunoglobulin only pairs the variable heavy chain of the first exogenous immunoglobulin, but not with the variable heavy chain of the second. exogenous immunoglobulin. Likewise, the variable light chain of the second exogenous immunoglobulin only pairs the variable heavy chain of the second exogenous immunoglobulin, but not with the variable heavy chain of the first exogenous immunoglobulin. Therefore, in certain embodiments, the present invention provides multimeric proteins which comprise at least one antigen binding site. In other embodiments the present invention provides heteromeric multimeric proteins which comprise at least one antigen binding site. In preferred embodiments said heteromeric multimeric proteins comprising at least one antigen binding site are immunoglobulins. In yet other embodiments said heteromeric multimeric proteins comprising at least one antigen binding site are functional fragments of an immunoglobulin. In yet other embodiments of the present invention said first and said second exogenous proteins are capable of forming a multimeric protein.

The term "antigen binding site" as used herein refers to any polypeptide stretch comprising a three-dimensional structure capable of specifically binding to an epitope. Such antigen binding site can comprise the VH and/or VL domain of an antibody or an immunoglobulin chain, preferably at least the VH domain. Such antigen binding site can also be comprised in a scFv. Antigen binding sites are also present on other proteinaceous molecules that are or may be used as scaffolds, such as proteins comprising fibronectin binding domains, anticalins, designed AR proteins (DARPins), T cell receptors, proteins comprising protein A domains, protein Z domains or Kunitz domains, Affibodys, ectoins, GFPs, cytochrome b562, adnectins, proteins of the Knottin family, gamma-crystallin and ubiquitin.

The present invention also provide methods for the production of more than two exogenous proteins in a eukaryotic host cell, wherein each of the genes encoding said proteins is under the control of a distinct inducible eukaryotic promoter, said method comprising the steps of (a) culturing said eukaryotic host cell under conditions that allow the expression of a gene encoding a first exogenous protein, (b) subsequently, culturing said eukaryotic host cell under conditions that allow the expression of a gene encoding a second exogenous protein, (c) subsequently, culturing said eukaryotic cell under conditions that allow the expression of a gene encoding a third exogenous protein, and, optionally, (d) subsequently, culturing said eukaryotic cell under conditions that allow the expression of even more genes encoding exogenous proteins. As will be evident the embodiments of the invention described herein above are also applicable to all scenario where more than two, such as three, four, five, ten, or more than ten exogenous protein are produced according to the present invention.

In yet other embodiments, the present invention provides a growth vessel for use in any of the methods provided in the present invention. The host cells of the present invention comprising the vectors or the vectors described herein above are grown in said growth vessels and the exogenous proteins are produced as described.

In yet other embodiments, the present invention provides a mixture of at least two exogenous proteins obtained by the methods of the present invention. In yet other embodiments, the present invention provides a mixture of at least two exogenous proteins obtainable by the methods of the present invention. Said mixture of at least two exogenous proteins is preferably a mixture of at least two immunoglobulins, such as a mixture of polyclonal antibodies or immunoglobulins and a mixture of oligoclonal antibodies or immunoglobulins.

In yet other embodiments, the present invention provides for the use of said mixture of at least two exogenous proteins obtained by or obtainable by the methods of the present invention in medicine. Preferably, said exogenous proteins are immunoglobulins and also preferably said use is use in the treatment of a disease. Depending on the nature and the antigen binding properties of the immunoglobulins, any disease may be treated. Preferred diseases are infectious diseases and cancer.

In yet other embodiments, the present invention provides host cells comprising the vector or the vectors as disclosed and described herein above. The host cells are capable of producing mixtures of at least two exogenous proteins. Preferably, said exogenous proteins are immunoglobulins, and most preferably said mixture of at least two exogenous proteins is a mixture of polyclonal or oligoclonal antibodies.

In yet other embodiments, the present invention provides vectors comprising the genes encoding said proteins under the control of said inducible eukaryotic promoters.

In yet other embodiments, the present invention provides a kit, comprising
(a) the host cells comprising the vector or the vectors of the present invention, and
(b) instructions to use said host cells in the methods described in the present invention. Said instructions may be provided in any suitable shape or form, such as written form, e.g. on paper, or in electronic from, such as a CD or any other electronic storage device.

EXAMPLES

Example 1

Generation of a Vector Suitable for Use in the Methods of the Present Invention

The gene encoding a first full length immunoglobulin is cloned behind a first inducible eukaryotic promoter, such that the expression of the first full length immunoglobulin is induced upon the addition of the inducer of said first inducible eukaryotic promoter. The tet promoter is used as the first inducible eukaryotic promoter. Expression from this promoter can be induced by the addition of tetracycline to the growth medium. Cloning occurs in a manner, so that the first full length immunoglobulin, including its inducible promoter, can be integrated into the genome of a host cell using the cre/lox system, i.e. the respective recognition sites are present on the vector.

Likewise, the gene encoding a second full length immunoglobulin is cloned behind a second inducible eukaryotic promoter, such that the expression of the second full length immunoglobulin is induced upon the addition of the inducer of said second inducible eukaryotic promoter. The first and the second inducible eukaryotic promoter are different. In particular, the inducer of the first inducible eukaryotic promoter does not lead to expression from the second inducible eukaryotic promoter, and the inducer of the second inducible eukaryotic promoter does not lead to expression from the first inducible eukaryotic promoter. The metallothionein promoter is used as the second inducible eukaryotic promoter. Expression from this promoter can be induced by the addition of copper or cadmium. Cloning occurs in a manner, so that the second full length immunoglobulin, including its inducible promoter, can be integrated into the genome of a host cell using the FlpIn system, i.e. the respective recognition sites are present on the vector.

The variable light and the variable heavy chain of the first full length immunoglobulin are under the control of the same first inducible eukaryotic promoter. Likewise, the variable light and the variable heavy chain of the second full length immunoglobulin are under the control of the same second inducible eukaryotic promoter. Between the variable light and the variable heavy chains, the respective nucleic acid stretches comprise additional ribosome binding sites to enable the separate translation of the respective variable chains.

Both full length immunoglobulins may be cloned in the same or on different vectors, using standard molecular cloning steps known to the skilled artisan. As an exemplary reference we refer to Maniatis et al, Molecular cloning: a laboratory manual (Cold Spring Harbour Laboratory Press).

Example 2

Transfection of the Vector into Suitable Host Cells

The host cell is transfected with the vector (if one vector comprises both full length immunoglobulins) or the vectors (if the two full length immunoglobulins are comprised on different vectors) generated in Example 1. HEK293 cells are used as host cells and the transfection is a stable transfection.

According to standard procedures the host cell population is selected for cells, into which both, the first and the second, full length immunoglobulins are stably integrated into the genome. One such clone of the host cell is selected and propagated for use in further experiments Example 3

Expression and Production of an Oligoclonal Mixture of Antibodies

The host cell comprising the first and the second full length immunoglobulin stable integrated in its genome is grown in an appropriate growth vessel. When a certain cell density is reached the inducer of the first inducible eukaryotic promoter, i.e. tetracycline, is added in amount sufficient to enable expression of said first full length immunoglobulin. Both the variable light and the variable heavy chain of the first immunoglobulin are produced, and the respective variable chains form an intact first full length immunoglobulin.

After the first full length immunoglobulin is produced at sufficient amounts, the inducer of the second inducible eukaryotic promoter, i.e. copper, is added in amount sufficient to enable expression of said second full length immunoglobulin. Both, the variable light and the variable heavy chain of the second immunoglobulin are produced, and the respective variable chains form an intact second full length immunoglobulin.

After the second full length immunoglobulin is produced at sufficient amounts, both full length immunoglobulins are purified from the culture broth by equivalent means known to the person skilled in the art.

Example 4

Use of the Oligoclonal Mixture of Antibodies in Therapy

The mixture of the two full length immunoglobulins is formulated appropriately. The resulting pharmaceutical preparation is used to treat patients in need thereof.

The invention claimed is:

1. A method for the production of at least two exogenous proteins in a mammalian or yeast host cell, wherein each of the genes encoding said proteins is under the control of a distinct inducible eukaryotic promoter, said method comprising
   (a) culturing a eukaryotic host cell under conditions that allow the expression of a gene encoding a first exogenous protein, and, subsequently,
   (b) culturing said eukaryotic host cell under conditions that allow the expression of a gene encoding a second exogenous protein, wherein said first and second exogenous proteins are immunoglobulins.

2. The method of claim 1, wherein during the expression of said gene encoding the first exogenous protein in step (a) said gene encoding the second exogenous protein is essentially not expressed.

3. The method of claim 1, wherein during the expression of said gene encoding the second exogenous protein in step (b) said gene encoding the first exogenous protein is essentially not expressed.

4. The method of claim 1, wherein said first and said second exogenous protein are encoded by genes on different vectors.

5. The method of claim 1, wherein said first and said second exogenous protein are encoded by genes on the same vector.

6. The method of claim 1, wherein one or both of said genes encoding said exogenous protein is/are introduced into said eukaryotic host cell via a stable transfection.

7. The method of claim 6, wherein said stable integration is affected by site specific integration.

8. The method of claim 7, wherein said side specific integration is site specific integration via the cre/lox system or via the Flp-In system.

9. The method of claim 1, wherein one or both of said genes encoding said exogenous proteins is/are introduced into said eukaryotic host cell via transient infection.

10. The method of claim wherein said inducible eukaryotic promoters are selected from hormone-responsive promoters, metal-responsive promoters, heat shock-responsive promoters, interferon-responsive promoters and antibiotic-responsive promoters.

11. The method of claim 10, wherein said promoter is selected from the tet promoter, the metallothionein promoter, the GRE promoter and the ecdyson promoter.

12. The method of claim 1, wherein said mammalian host cell is selected from a CHO cell, a PER.C6 cell, a HKB1 1 cell, and a HEK293 cell.

13. The method of claim 1, further comprising the step(s) of
   (c) culturing said eukaryotic cell under conditions that allow the expression of a gene encoding a third exogenous protein.

* * * * *